(12) United States Patent
Cheng et al.

(10) Patent No.: US 11,315,677 B2
(45) Date of Patent: Apr. 26, 2022

(54) DETECTION MODEL TRAINING METHOD AND APPARATUS, AND TERMINAL DEVICE

(71) Applicant: TENCENT TECHNOLOGY (SHENZHEN) COMPANY LIMITED, Shenzhen (CN)

(72) Inventors: Chen Cheng, Shenzhen (CN); Zhongqian Sun, Shenzhen (CN); Hao Chen, Shenzhen (CN); Wei Yang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 14 days.

(21) Appl. No.: 17/084,475

(22) Filed: Oct. 29, 2020

(65) Prior Publication Data
US 2021/0043306 A1    Feb. 11, 2021

Related U.S. Application Data

(63) Continuation of application No. PCT/CN2019/090521, filed on Jun. 10, 2019.

(30) Foreign Application Priority Data

Oct. 25, 2018   (CN) .......................... 201811251214.0

(51) Int. Cl.
*G06K 9/00* (2022.01)
*G16H 30/40* (2018.01)
(Continued)

(52) U.S. Cl.
CPC .......... *G16H 30/40* (2018.01); *G06K 9/6232* (2013.01); *G06K 9/6256* (2013.01);
(Continued)

(58) Field of Classification Search
CPC .......... G06K 2209/051; G06K 9/4628; G06K 9/6232; G06K 9/6256; G06K 9/6267;
(Continued)

(56) References Cited

U.S. PATENT DOCUMENTS

| 2014/0136453 A1 | 5/2014 | Morimura |
| 2018/0060722 A1 | 3/2018 | Hwang et al. |

FOREIGN PATENT DOCUMENTS

| CN | 106469560 A | 3/2017 |
| CN | 107704926 A | 2/2018 |

(Continued)

OTHER PUBLICATIONS

The State Intellectual Property Office of the People's Republic of China (SIPO) Office Action 1 for for 201811251214.0 dated Mar. 3, 2021 10 Pages (including translation).

(Continued)

*Primary Examiner* — Xin Jia
(74) *Attorney, Agent, or Firm* — Anova Law Group, PLLC

(57) ABSTRACT

The present application discloses a detection model training method and apparatus. The method includes determining an initial training model; determining a training sample; determining whether a lesion target is present in a first user body organ image through the initial detection model according to a feature of the each first user body organ image, to obtain a detection result; and determining a domain that each user body organ image in the training sample belongs to through the adaptive model according to a feature of the each user body organ image, to obtain a domain classification result; calculating, a loss function value related to the initial training model according to the detection result, the domain classification result, a first identifier, a second identifier, and a third identifier; and adjusting a parameter value in the (Continued)

initial training model according to the loss function value, to obtain a final detection model.

20 Claims, 5 Drawing Sheets

(51) Int. Cl.
| | |
|---|---|
| *G16H 30/20* | (2018.01) |
| *G16H 50/20* | (2018.01) |
| *G06K 9/62* | (2022.01) |
| *G06N 3/08* | (2006.01) |

(52) U.S. Cl.
CPC .............. *G06K 9/6267* (2013.01); *G06N 3/08* (2013.01); *G16H 30/20* (2018.01); *G16H 50/20* (2018.01)

(58) Field of Classification Search
CPC ...... G06K 9/6271; G06N 3/0454; G06N 3/08; G16H 30/20; G16H 30/40; G16H 50/20
See application file for complete search history.

(56) References Cited

FOREIGN PATENT DOCUMENTS

| | | |
|---|---|---|
| CN | 108062753 A | 5/2018 |
| CN | 108399431 A | 8/2018 |
| CN | 108460415 A | 8/2018 |
| CN | 109447149 A | 3/2019 |
| JP | 2014096039 A | 5/2014 |
| JP | 2018121886 A | 8/2018 |

OTHER PUBLICATIONS

The World Intellectual Property Organization (WIPO) International Search Report for PCT/CN2019/090521 dated Sep. 10, 2019 7 Pages (including translation).

Nuh Hatipoglu et al., "Classification of Histopathological Images Using Convolutional Neural Network," IEEE Image Processing Theory, Tools and Applications, Dec. 31, 2014 (Dec. 31, 2014), entire document. 6 pages.

Ross Girshick et al., "Rich Feature Hierarchies for Accurate Object Detection and Semantic Segmentation," 2014 IEEE Conference on Computer Vision and Pattern Recognition, Dec. 31, 2014 (Dec. 31, 2014), entire document. 8 pages.

The European Patent Office (EPO) The Extended European Search Report for 19877123.0 dated Nov. 9, 2021 13 Pages.

Konstantinos Kamnitsas et al., "Unsupervised domain adaptation in brain lesion segmentation with adversarial networks," ARXIV. ORG, arXiv:1612.08894v1, Dec. 28, 2016 (Dec. 28, 2016). 13 pages.

Yaroslav Ganin et al: "Domain-Adversarial Training of Neural Networks," ARXIV.ORG, arXiv:1505.07818v4, May 26, 2015 (May 26, 2015). 35 pages.

Jiali Liu et al., "Integrate Domain Knowledge in Training CNN for Ultrasonography Breast Cancer Diagnosis," Springer Nature Switzerland AG 2018, A.F.Frangi et al. (Eds.): MICCAI 2018, LNCS 11071, Sep. 26, 2018 (Sep. 26, 2018), pp. 868-875. 8 pages.

The Japan Patent Office (JPO) Notification of Reasons for Refusal for Application No. 2020-562170 and Translation Jan. 18, 2022 44 pages.

Konstantinos Kamnitsas et al., "Unsupervised domain adaptation in brain lesion segmentation with adversarial networks," arXiv:1612.08894v1, Dec. 28, 2016. 13 pages.

Yaroslav Ganin et al., "Domain-Adversarial Training of Neural Networks", arXiv:1505.07818v4, May 26, 2016. 35 pages.

DETECTION MODEL TRAINING METHOD AND APPARATUS, AND TERMINAL DEVICE

RELATED APPLICATIONS

This application is a continuation application of PCT Application No. PCT/CN2019/090521, which in turn claims priority to Chinese Patent Application No. 201811251214.0, entitled "DETECTION MODEL TRAINING METHOD AND APPARATUS, AND TERMINAL DEVICE," filed with the National Intellectual Property Administration on Oct. 25, 2018. The two applications are both incorporated herein by reference in their entirety.

FIELD OF THE TECHNOLOGY

This application relates to the field of information processing technologies, and in particular, to a detection model training method and apparatus, and a terminal device.

BACKGROUND OF THE DISCLOSURE

In recent years, artificial intelligence has played an increasingly significant role in the field of medical imaging. The colorectal polyp detection system based on deep learning methods can learn and train millions of pieces of gold standard colorectal data, and assist clinicians in diagnosis, to reduce the omission rate.

In a colorectal polyp detection system, a convolutional neural network is used to perform feature extraction on a to-be-examined image, and then to perform classification by using the support vector machine method. When the support vector machine method is used for performing the classification, first, it is determined whether there is a polyp in the to-be-examined image, and then qualitative classification is performed on the polyp in the to-be-examined image.

Data used during training of the convolutional neural network and the support vector machine are private data. The amount of the training data is small, and the obtained detection results of the system is unsatisfactory. In addition, because different hospitals use different devices and different doctors have different operating habits, there is a difference between image data acquired from different hospitals. For example, the image data differ in the resolution and background noise of the image. As a result, when the colorectal polyp detection system is deployed in different hospitals, the detection accuracy is greatly reduced.

By collecting more training data from more hospitals, the situation can be improved to some extent. However, to obtain colorectal data in training data, a training picture needs to be labeled by a professional physician, and collecting more data is enormously expensive and time-consuming.

SUMMARY

Embodiments of this application provide a detection model training method and apparatus, and a terminal device, so that a final detection model is trained according to an initial detection model and an adaptive model.

One aspect of the embodiments of this application provides a detection model training method. The method includes determining, by a training apparatus, an initial training model, the initial training model comprising an initial detection model and an adaptive model; and determining, by the training apparatus, a training sample, the training sample comprising source domain data and target domain data, the source domain data comprising a plurality of first user body organ images, each first user body organ image comprising: a first identifier of whether a lesion target is present, and a second identifier of a domain that the each first user body organ image belongs to; the target domain data comprising: a plurality of second user body organ images, and a third identifier of a domain that each second user body organ image belongs to. The method further includes determining, by the training apparatus, whether a lesion target is present in the each first user body organ image through the initial detection model according to a feature of the each first user body organ image, to obtain a detection result; and determining, by the training apparatus, a domain that each user body organ image in the training sample belongs to through the adaptive model according to a feature of the each user body organ image, to obtain a domain classification result; calculating, by the training apparatus, a loss function value related to the initial training model according to the detection result, the domain classification result, the first identifier, the second identifier, and the third identifier; and adjusting, by the training apparatus, a parameter value in the initial training model according to the loss function value, to obtain a final detection model.

Another aspect of the embodiments of this application provides a training apparatus. The training apparatus includes a model determining unit, configured to determine an initial training model, the initial training model comprising an initial detection model and an adaptive model; a sample determining unit, configured to determine a training sample, the training sample comprising source domain data and target domain data, the source domain data comprising a plurality of first user body organ images, each first user body organ image comprising: a first identifier of whether a lesion target is present, and a second identifier of a domain that the each first user body organ image belongs to; the target domain data comprising: a plurality of second user body organ images, and a third identifier of a domain that each second user body organ image belongs to; a model processing unit, configured to separately determine whether a lesion target is present in the each first user body organ image through the initial detection model according to a feature of the each first user body organ image, to obtain a detection result; and separately determine a domain that each user body organ image in the training sample belongs to through the adaptive model according to a feature of the each user body organ image, to obtain a domain classification result; a loss function unit, configured to calculate a loss function value related to the initial training model according to the detection result, the domain classification result, the first identifier, the second identifier, and the third identifier; and an adjustment unit, configured to adjust a parameter value in the initial training model according to the loss function value, to obtain a final detection model.

Another aspect of the embodiments of this application provides a non-transitory storage medium, the storage medium storing a plurality of instructions, the instructions being adapted to be loaded by a processor and cause the processor to perform: determining an initial training model, the initial training model comprising an initial detection model and an adaptive model; determining a training sample, the training sample comprising source domain data and target domain data, the source domain data comprising a plurality of first user body organ images, each first user body organ image comprising: a first identifier of whether a lesion target is present, and a second identifier of a domain that the each first user body organ image belongs to; the target domain data comprising: a plurality of second user body organ images, and a third identifier of a domain that each second user body organ image belongs to; determining whether a lesion target is present in the each first user body organ image through the initial detection model according to a feature of the each first user body organ image, to obtain a detection result; and determining a domain that each user body organ image in the training sample belongs to through the adaptive model according to a feature of the each user body organ image, to obtain a domain classification result; calculating a loss function value related to the initial training model according to the detection result, the domain classification result, the first identifier, the second identifier, and the third identifier; and adjusting a parameter value in the initial training model according to the loss function value, to obtain a final detection model.

Another aspect of the embodiments of this application provides a terminal device. The terminal device includes a processor and a storage medium, the processor being configured to implement instructions. The storage medium being configured to store a plurality of instructions, the instructions being loaded by the processor to perform: determining an initial training model, the initial training model comprising an initial detection model and an adaptive model; determining a training sample, the training sample comprising source domain data and target domain data, the source domain data comprising a plurality of first user body organ images, each first user body organ image comprising: a first identifier of whether a lesion target is present, and a second identifier of a domain that the each first user body organ image belongs to; the target domain data comprising: a plurality of second user body organ images, and a third identifier of a domain that each second user body organ image belongs to; determining whether a lesion target is present in the each first user body organ image through the initial detection model according to a feature of the each first user body organ image, to obtain a detection result; and determining a domain that each user body organ image in the training sample belongs to through the adaptive model according to a feature of the each user body organ image, to obtain a domain classification result; calculating a loss function value related to the initial training model according to the detection result, the domain classification result, the first identifier, the second identifier, and the third identifier; and adjusting a parameter value in the initial training model according to the loss function value, to obtain a final detection model.

In embodiments of the present application, when training a detection model used for detecting a lesion target in a user body organ image, the training apparatus first determines that an initial training model includes an initial detection model and an adaptive model, and includes source domain data labeled with lesion target information and target domain data not labeled with lesion target information. Then, the training apparatus processes data in a training sample according to the initial detection model and the adaptive model, to obtain a detection result and a domain classification result respectively. Finally, the training apparatus calculates a related loss function value according to the detection result, the domain classification result, and the training sample, and adjusts a certain parameter value in the initial training model according to the loss function value, to obtain a final detection model. Accordingly, in a process of training the detection model, some of data of the training sample is the source domain data labeled with the lesion target information, and the remaining data of the training sample is the target domain data not labeled with the lesion target information, so that an image not labeled with the lesion target information can also be used as a training sample when it is difficult and/or costly to label lesion target information. Therefore, the training sample size is increased, and the detection model obtained through training is more accurate.

BRIEF DESCRIPTION OF THE DRAWINGS

To describe the technical solutions of the embodiments of this application more clearly, the following briefly describes the accompanying drawings required for describing the embodiments. Apparently, the accompanying drawings in the following description show only some embodiments of this application, and a person of ordinary skill in the art may still derive other drawings from the accompanying drawings without creative efforts.

DESCRIPTION OF EMBODIMENTS

The technical solutions in the embodiments of this application are clearly described in the following with reference to the accompanying drawings in the embodiments of this application. Apparently, the embodiments to be described are merely some embodiments of this application rather than all of the embodiments. All other embodiments obtained by a person of ordinary skill in the art based on the embodiments of this application without making creative efforts shall fall within the protection scope of this application.

In the specification, claims, and accompanying drawings of this application, the terms "first", "second", "third", "fourth", and so on (if existing) are intended to distinguish between similar objects rather than describe a specific order or sequence. It may be understood that the data termed in such a way is interchangeable in proper circumstances, so that the embodiments of this application described herein for example, can be implemented in other orders than the order illustrated or described herein. Moreover, the terms "include", "comprise" and any other variations mean to cover the non-exclusive inclusion. For example, a process, method, system, product, or device that includes a list of operations or units is not necessarily limited to those expressly listed steps or units, but may include other steps or units not expressly listed or inherent to such a process, method, system, product, or device.

Figure 1:
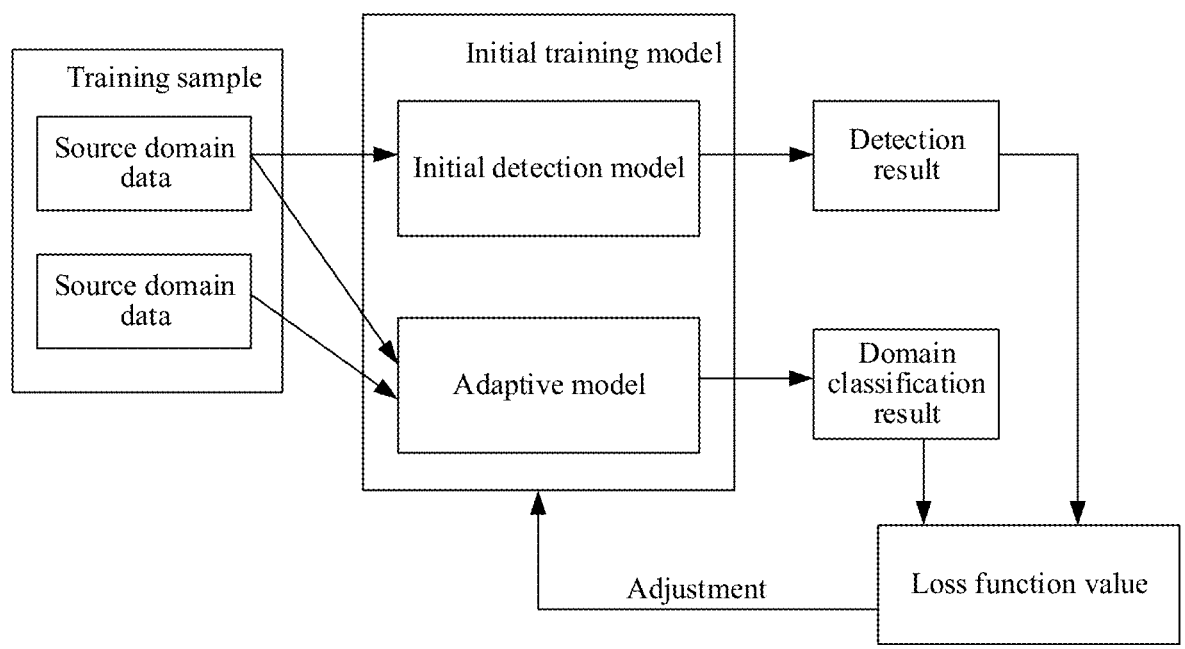
FIG. 1 is a schematic diagram of a detection model training method according to an embodiment of this application.

An embodiment of this application provides a detection model training method, mainly applied to a training apparatus. Referring to FIG. 1, the training apparatus may train a detection model through the following steps: determining an initial training model, the initial training model including an initial detection model and an adaptive model; determining a training sample, the training sample including source domain data and target domain data, the source domain data including a plurality of first user body organ images, each first user body organ image including: a first identifier of whether a lesion target is present, and a second identifier of a domain that the each first user body organ image belongs to; the target domain data including: a plurality of second user body organ images, and a third identifier of a domain that each second user body organ image belongs to; separately determining whether a lesion target is present in the each first user body organ image through the initial detection model according to a feature of the each first user body organ image, to obtain a detection result; and separately determining a domain that each user body organ image in the training sample belongs to through the adaptive model according to a feature of the each user body organ image, to obtain a domain classification result; calculating a loss function value related to the initial training model according to the detection result, the domain classification result, the first identifier, the second identifier, and the third identifier; and adjusting a parameter value in the initial training model according to the loss function value, to obtain a final detection model.

Accordingly, in a process of training the detection model, some of data of the training sample is the source domain data labeled with the lesion target information, and the remaining data of the training sample is the target domain data not labeled with the lesion target information, so that an image not labeled with the lesion target information can also be used as a training sample in a case that it is difficult to label lesion target information. Therefore, the amount of training sample increases, and the detection model obtained through training is more accurate.

Figure 2:
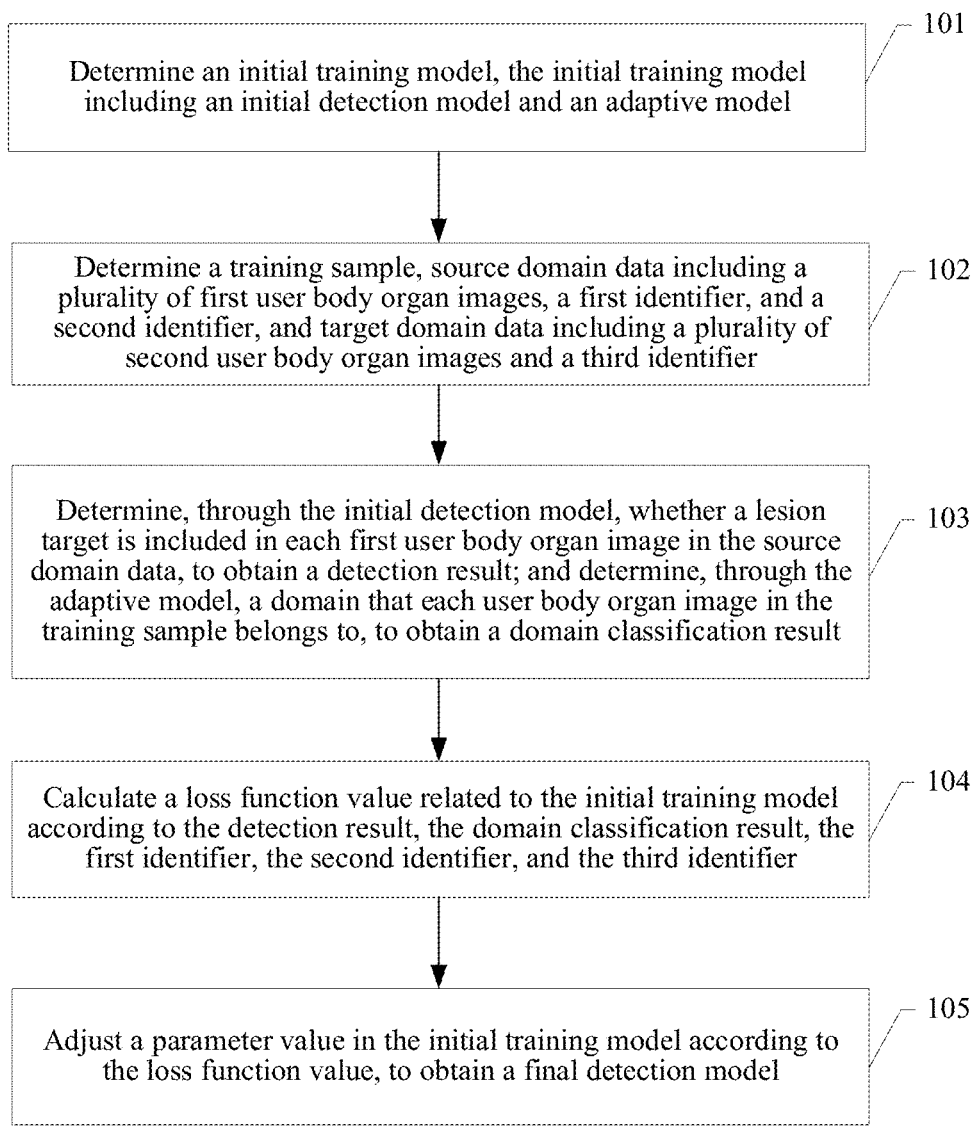
FIG. 2 is a flowchart of a detection model training method according to an embodiment of this application.

An embodiment of this application provides a detection model training method, mainly performed by a training apparatus. A detection model obtained through training by the training apparatus is mainly used for detecting whether an image includes a lesion target of a body. A flowchart may be shown in FIG. 2, and the method includes the following steps:

Step 101: Determine an initial training model, the initial training model including an initial detection model and an adaptive model.

It may be understood that a user may operate the training apparatus, so that the training apparatus initiates training for the detection model in this embodiment. When determining the initial training model, the training apparatus determines a multilayer structure included in the initial detection model and an initial value of a certain parameter in each layer of the structure. The multilayer structure in the initial detection model may be any one of the following algorithm structures: a convolutional neural network (CNN) structure, a K nearest neighbors (KNN) structure, a singular value decomposition (SVD) structure, a non-negative matrix factorization (NMF) structure, or the like.

In some embodiments, the initial detection model determined by the training apparatus may include a feature extraction module and a detection and classification module, and the adaptive model includes a domain classification module. The feature extraction module is configured to extract a feature. The detection and classification module is configured to perform classification of whether a lesion target is present according to a feature extracted by the feature extraction module. The domain classification module is configured to perform domain classification according to the feature extracted by the feature extraction module.

Accordingly, the feature extracted by the feature extraction module is shared between the initial detection model and the adaptive model.

Further, the training apparatus further determines an initial value of a certain parameter in the initial detection model and the adaptive model. The certain parameter herein is a certain parameter that is used in a calculation process of each layer of the structure in the initial training model and that does not need to be assigned with a value at any time, such as a weight, an angle, or the like.

In one embodiment, the adaptive model may further include a gradient inversion module. The gradient inversion module is configured to transfer the feature extracted by the feature extraction module to the domain classification module, and is further configured to reverse, in a case that the certain parameter value is adjusted, an error of the domain classification module (for example, multiply the error of the domain classification module by a negative number), to adjust the certain parameter value in the feature extraction module according to the reversed error.

Accordingly, because a training process is a process of continuously optimizing the certain parameter in the initial training model, the feature extraction module and the gradient inversion module form an adversarial relationship in the training process. Optimization of the certain parameter in the feature extraction module causes an increase of an error of the domain classification module, while through the gradient inversion module, the error of the domain classification module decreases until the error tends to be in a balanced state.

Step 102: Determine a training sample, the training sample including source domain data and target domain data, the source domain data including a plurality of first user body organ images, each first user body organ image including: a first identifier of whether a lesion target is present, and a second identifier of a domain that the each first user body organ image belongs to; the target domain data including: a plurality of second user body organ images, and a third identifier of a domain that each second user body organ image belongs to.

Further, for some of the first user body organ images, the some of the user body organ images include lesion targets, and the source domain data further includes types and locations of the lesion targets included in the some of the user body organ images.

Step 103: Determine whether a lesion target is present in the each first user body organ image through the initial detection model according to a feature of the each first user body organ image, to obtain a detection result; and determine a domain that each user body organ image (including the first user body organ image and the second user body organ image) in the training sample belongs to through the adaptive model according to a feature of the each user body organ image, to obtain a domain classification result.

Further, if the source domain data includes types and locations of the lesion targets included in the some of the user body organ images, the types and the locations of the lesion targets included in the some of the user body organ images further need to be determined through the initial detection model separately, to obtain a target detection result.

Step 104: Calculate a loss function value related to the initial training model according to the detection result, the domain classification result, the first identifier, the second identifier, and the third identifier.

The loss function related to the initial training model herein may include a detection loss function and an adaptive loss function, and an overall loss function of the foregoing initial training model may include a function calculated value of the detection loss function and the adaptive loss function, for example, a weighted sum value. The detection loss function includes: a difference, that is, a first error between information that is determined according to the initial detection model in the initial training model and that is about whether the lesion targets are included in the first user body organ images and whether the lesion targets are actually included in the first user body organ images (that is, the first identifier included in the source domain data). The adaptive loss function includes: a difference, that is, a second error between information that is determined according to the adaptive model in the initial training model and that is about whether the each user body organ image in the training sample belongs to a source domain or a target domain, and information about that the each user body organ image actually belongs to a domain (that is, the second identifier and the third identifier).

Further, the detection loss function further includes: a difference, that is, a third error between the types and the locations that are of the lesion targets in the some of the user body organ images and that are determined according to the initial detection model in the initial training model and the actual types and the actual locations of the lesion targets in the some of the user body organ images (that is, the types and the locations labeled in the source domain data included in the training sample). Accordingly, the detection loss function may include a function calculated value of the first error, the third error, and the second error, for example, a weighted sum value.

In a mathematical representation form of the first error, the second error, or the third error, a cross entropy is usually used for establishing a loss function, and a training process of the detection model is to minimize values of the errors. The training process is to continuously optimize the initial value of the certain parameter determined in step 102 through a series of mathematical optimization methods such as back propagation derivation and gradient descent, and minimize a calculated value of the function. Therefore, after performing this step 104, the training apparatus needs to perform an adjustment step in step 105.

Step 105: Adjust a certain parameter value in the initial training model according to the loss function value, to obtain a final detection model.

In some embodiments, if a calculated function value of the loss function is relatively large, for example, greater than a preset value, the certain parameter value needs to be changed, for example, a weight value of a weight is decreased, to decrease the function value that is of the loss function and that is calculated according to an adjusted certain parameter value.

Steps 103 to 105 are an adjustment on the certain parameter value in the initial training model according to the detection result and the domain classification result that are obtained after the user body organ images in the training sample are processed through the initial training model. In some embodiments, steps 103 to 105 need to be performed continuously and circularly until the adjustment to the certain parameter value meets a specific stop condition.

Therefore, after performing steps 101 to 105 in the foregoing embodiment, the training apparatus further needs to determine whether a current adjustment to the certain parameter value meets a preset stop condition. If yes, the process ends; if not, for the initial training model of which the certain parameter value is adjusted, the training apparatus returns to perform steps 103 to 105.

The preset stop condition includes, but is not limited to any one of the following conditions: a difference between a currently adjusted certain parameter value and a last adjusted certain parameter value is less than a threshold, that is, the adjusted certain parameter value reaches convergence; and a quantity of times of the adjustment to the certain parameter value reaches a preset quantity of times.

Further, when detecting a to-be-examined user body organ image after determining a final detection model, the training apparatus first determines a to-be-examined user body organ image, then determines whether a lesion target is present in the to-be-examined user body organ image directly according to the final detection model, and determines, if a lesion target is present, a type and a location of the lesion target. When the to-be-examined user body organ image is determined, an original image of the user body organ may be determined first, and then the original image may be preprocessed, for example, enhanced and denoised, to obtain a to-be-examined user body organ image, so that detection of the to-be-examined user body organ image according to the final detection model is not affected by defects of the image itself.

In the method of this embodiment, when training a detection model used for detecting a lesion target in a user body organ image, the training apparatus first determines that an initial training model includes an initial detection model and an adaptive model, and includes source domain data labeled with lesion target information and target domain data not labeled with lesion target information. The training apparatus then processes data in a training sample according to the initial detection model and the adaptive model, to obtain a detection result and a domain classification result respectively. Finally, the training apparatus calculates a related loss function value according to the detection result, the domain classification result, and the training sample, and adjusts a certain parameter value in the initial training model according to the loss function value, to obtain a final detection model. Accordingly, in a process of training the detection model, some of data of the training sample is the source domain data labeled with the lesion target information, and the remaining data of the training sample is the target domain data not labeled with the lesion target information, so that an image not labeled with the lesion target information can also be used as a training sample in a case that it is difficult to label lesion target information. Therefore, the amount of usable training samples is increased, and the detection model obtained through training is more accurate.

Figure 3:
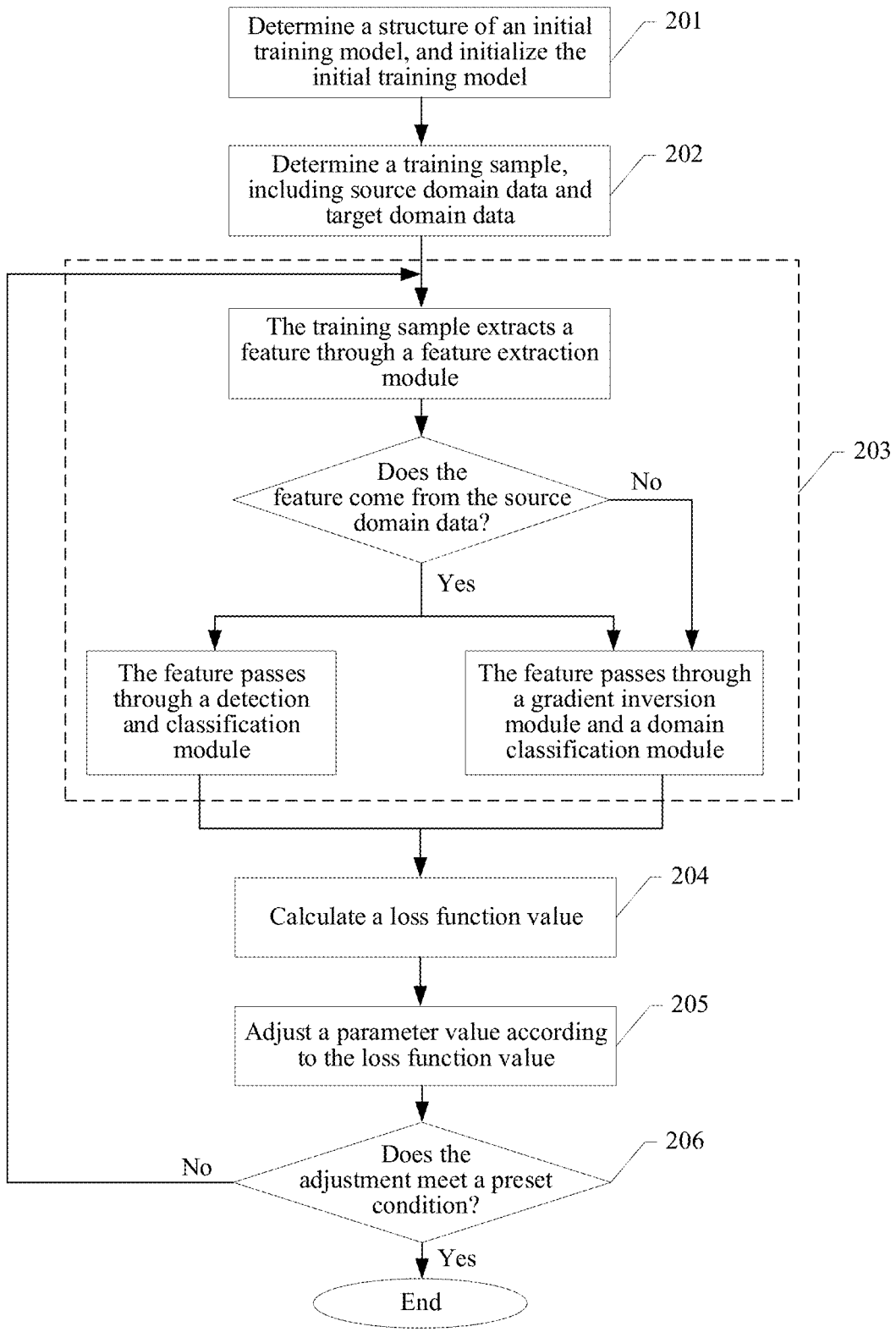
FIG. 3 is a flowchart of a detection model training method according to an application embodiment of this application.

The detection model training method in this embodiment is described below by using a specific application example. The method in this embodiment is applied to detection of polyps in a colorectal image. The method in this embodiment may include the following two parts:

1. Referring to FIG. 3, Training of the Detection Model May Include the Following Steps:

Step 201: Determine an initial training model.

Figure 4:
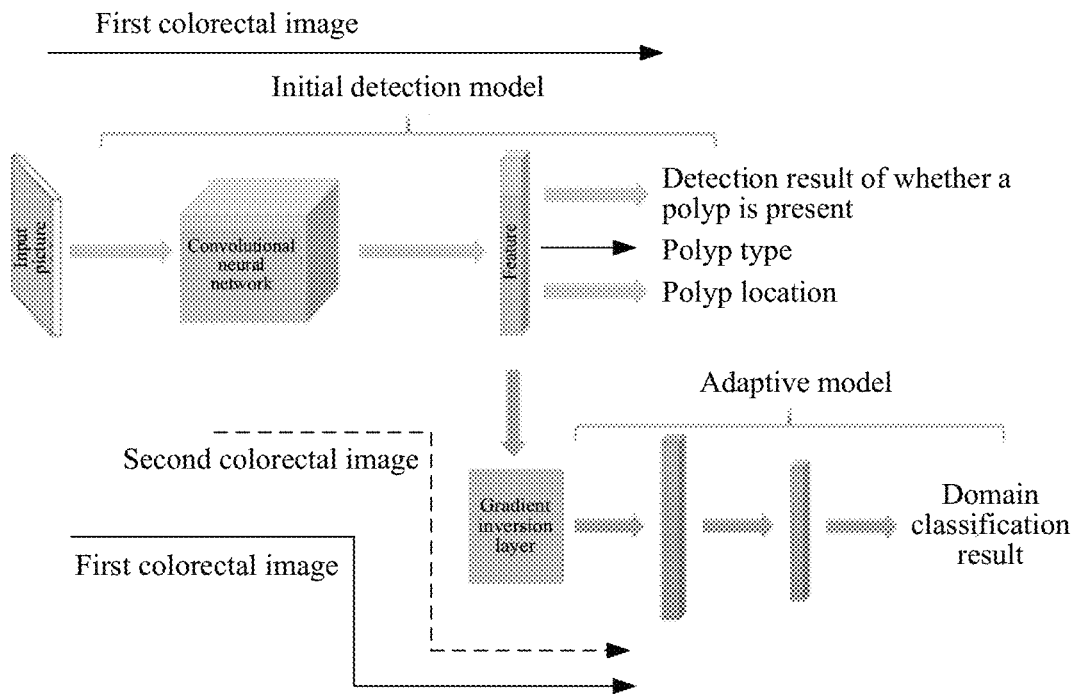
FIG. 4 is a schematic diagram of an initial training model determined according to an application embodiment of this application.

Referring to FIG. 4, the training apparatus may first determine that a structure of the initial training model includes: an initial detection model and an adaptive model, where the initial detection model includes a feature extraction module (that is, a convolutional neural network shown in FIG. 4) and a detection and classification module, and the adaptive model includes a gradient inversion module (that is, a gradient inversion layer shown in FIG. 4) and a domain classification module. The gradient inversion module may be connected to a final feature extraction module of the feature extraction module, or may be connected to an intermediate feature extraction module of the feature extraction module.

Then, the training apparatus initializes a determined initial training model, that is, determines initial values of certain parameters in the initial training model.

For example, if the initial detection model is a CNN algorithm structure, a multilayer structure of the determined initial detection model may include a convolutional layer and a pooling layer (that is, the feature extraction module), and a fully connected layer and a normalization layer (that is, the detection and classification module). The convolutional layer is used for extracting all features of an input image. The pooling layer is used for sampling and calculating all the features obtained by the convolutional layer, to obtain key features in the input image; the fully connected layer is used for calculating, according to sampled features, a fraction that each input picture belongs to a specific type. The normalization layer is used for outputting, according to the fraction calculated by the fully connected layer, a probability that an input picture belongs to a specific type. In this embodiment, any colorectal image is used as the input picture.

In this case, the pooling layer is the final feature extraction module of the feature extraction module, and can obtain final key features of the input image, thereby simplifying subsequent calculations. The convolutional layer is the intermediate feature extraction module of the feature extraction module, and may obtain all the features of the input picture. The certain parameters corresponding to the initial detection model may include: calculated parameters in a convolution kernel, a pooling kernel, and the fully connected layer, for example, a weight value.

Step 202: Determine a training sample, the training sample including source domain data and target domain data, the source domain data including a plurality of first colorectal images (that is, user body organ images), each first colorectal image including: a first identifier of whether a polyp (that is, a lesion target) is included, types and locations of polyps of some of colorectal images (colorectal images including polyps), and a second identifier of a domain that the each first colorectal image belongs to. The target domain data including: a plurality of second colorectal images, and a third identifier of a domain that each second colorectal image belongs to.

In this case, polyp information in the first colorectal images is labeled in the source domain data, while polyp information in second colorectal images is not labeled in the target domain data.

Step 203: For the source domain data in the training sample, the initial detection model separately extracts a feature of each first colorectal image, and separately determines whether a polyp is included in the each first colorectal image according to the feature of the each first colorectal image, to obtain a detection result; and for the colorectal images including polyps, the initial detection model needs to detect a type and a location of the each first colorectal image separately, to obtain a target detection result.

For the target domain data in the training sample, the adaptive model directly separately determines information about the domain that the each second colorectal image belongs according to the each second colorectal image, to obtain a domain classification result. In a specific implementation, for any second colorectal image, after the feature of the second colorectal image is extracted through the final feature extraction module or the intermediate feature extraction module in the feature extraction module of the initial detection model, the feature of the second colorectal is transferred to the domain classification module through the gradient inversion module, and then the domain classification module performs domain classification according to the feature of the second colorectal image. In this process, the gradient inversion module performs no processing on the feature of the second colorectal.

As shown in FIG. 4, in a training process, the direction of the first colorectal image is indicated by the solid arrows in the figure. The first colorectal image needs to pass through the initial detection model, and also needs to pass through the gradient inversion module and the domain classification module in the adaptive model. The direction of the second colorectal image is indicated by the dotted arrow in the figure. The second colorectal image passes through the feature extraction module in the initial detection model and the gradient inversion module and the domain classification module in the adaptive model.

In some embodiments, after a corresponding feature is extracted from each colorectal image in the training sample through the feature extraction module, if the feature comes from the source domain data, the extracted feature needs to be processed by the detection and classification module, the gradient inversion module, and the domain classification module separately; if the feature comes from the target domain data, the extracted feature only needs to be processed by the gradient inversion module and the domain classification module.

Accordingly, the feature extraction module extracts common features from different domain data, eliminates domain-related features, and eliminates differences between the target domain data and the source domain data, so that features extracted from the target domain data and the source domain data have domain invariance, and further, classification and detection capabilities learned from the source domain data can be directly applied to the target domain data.

Step 204: Calculate a loss function value related to the initial training model according to the detection result, the target detection result, the domain classification result, the first identifier, the second identifier, and the third identifier that are obtained.

In some embodiments, the loss function value related to the initial training model includes: a function calculated value of a loss function of the initial detection model and a loss function of the adaptive model. The loss function of the initial detection model may include: a detection loss function L1 (that is, the foregoing first error), a classification loss function Las, and a positioned regression loss function $L_{box}$ (that is, the foregoing third error). Accordingly, an overall loss function value of the initial detection model may be expressed by the following formula 1, where $\lambda 1$ and $\lambda 2$ are constants used for balancing the detection loss function, the classification loss function, and the positioned regression loss function:

$$L_{det}=L1/\lambda 1*L_{cls}+\lambda 2*L_{box} \quad (1)$$

The loss function of the adaptive model (that is, the foregoing second error) may be expressed by the cross entropy of the following formula 2. When $D_i$ is 0, an input picture is the source domain data, and when $D_i$ is 1, the input picture is the target domain data. Data. $p_i$ represents a probability that a final output of the domain classification module is the source domain data:

$$L_d=\Sigma(D_i \log(p_i)+(1-D_i)\log(1-p_i)) \quad (2)$$

Therefore, the loss function related to the initial training model may be expressed by the following formula 3, where β is used for balancing the loss function of the adaptive model and the loss function of the initial detection model:

$$L = L_{det} + \beta \cdot L_d \quad (3)$$

Step 205: Adjust a certain parameter value in the initial training model according to the loss function value.

After the overall loss function value is calculated through the foregoing step 204, the training apparatus may update the initial value (mainly the weight value) of the certain parameter of the initial training model layer by layer. In a process of updating the weight value, the following two cases may be mainly included:

(1) For Modules Other than the Gradient Inversion Module in the Initial Training Model When updating weight values of the modules other than the gradient inversion module, the training apparatus updates the weight values layer by layer from back to front. For example, weight values in the detection and classification module and the domain classification model are updated first, and then the weight value in the feature extraction module is updated. When a weight value of a layer is updated, a gradient may be calculated according to a correspondence between a loss function value L and a weight value w, and then the weight value of the layer is updated toward the direction of the gradient to minimize the error. For example, the gradient is dL/dw2, where w2 is a weight value before the update, then the updated weight value w1=w2−learning_rate*dL/dw, where learning_rate is a learning rate used for controlling a step size of each weight value change.

If a layer is a module of a last layer, during calculation of a gradient of the layer, the loss function value L may be directly used as the error of the layer to calculate the gradient. If a layer is not the module of the last layer, during calculation of a gradient of the layer, a product of an error of a previous layer and the weight value of this layer needs to be used as the error of this layer to calculate the gradient. An order from the previous layer to this layer is an order from back to front in the initial training model.

(2) For the Gradient Inversion Module

The gradient inversion module does not include any certain parameter such as a weight value. The training apparatus first determines an error of a previous layer of module of the gradient inversion module (that is, the domain classification module). Then, the gradient inversion module multiplies the error by a negative number to obtain a gradient, and uses the gradient as an error of a subsequent layer of module of the gradient inversion module, to implement an inversion of the subsequent module of the gradient inversion module, that is, the gradient of the feature extraction module, thereby maximizing the error of the domain classification module.

Accordingly, an objective of the feature extraction module in the initial detection model is that the domain classification module makes as many mistakes as possible during classification, while the adaptive module is to make the domain classification module make as few mistakes as possible during classification, thereby eventually reaching a balance. Accordingly, features extracted by the feature extraction module do not include domain-related feature information, so that differences between different domains can be eliminated, and a phenomenon of domain migration can be eliminated.

Figure 5:
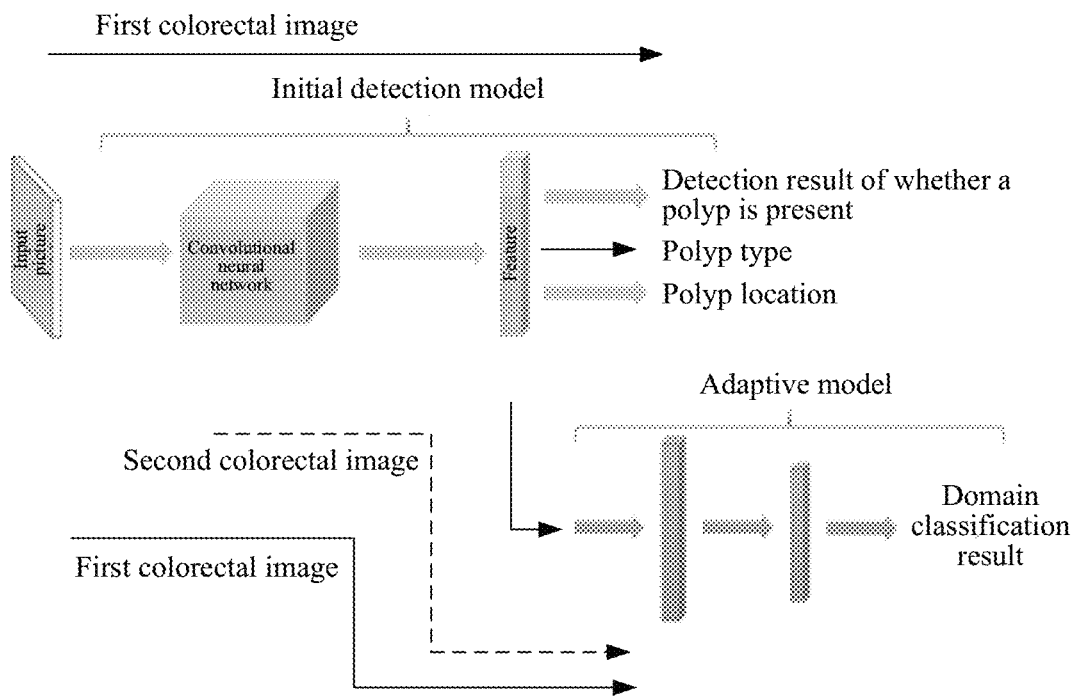
FIG. 5 is a schematic diagram of another initial training model determined according to an application embodiment of this application.

The features extracted by the feature extraction module in the determined initial training model pass through the gradient inversion module and reach the domain classification module. As shown in FIG. 5, in another embodiment, the determined initial training model may not include the gradient inversion module, so that the features extracted by the feature extraction module do not pass through the gradient inversion module. In this case, the training apparatus needs to adjust a weight value in the domain classification module, and then perform the method performed by the foregoing gradient inversion module, to implement the inversion of the gradient of the feature extraction module.

Step 206: Determine whether the adjustment to the certain parameter value meets any one of the following preset conditions: a quantity of times of the adjustment to the certain parameter value reaches a preset quantity of times, and a difference between a currently adjusted certain parameter value and a last adjusted certain parameter value is less than a threshold; if not, return to perform step 203; if yes, the process ends.

By continuously repeating the foregoing steps 203 to 206, the final detection model can be obtained.

Because information about polyps in colorectal images needs to be labeled by a professional physician, which is extremely expensive and time-consuming, and different hospitals use different devices, resulting in large differences in the distribution of colorectal image data. Consequently, collected training data cannot cover all hospitals. In the embodiments of this application, to apply the adaptive model to the detection model for colorectal images, only existing labeled source domain data (including the first colorectal images), combined with image data of a new hospital, that is, the target domain data (including the second colorectal images) is required, without a need to label the polyps in the target domain data, so that detection of the first colorectal images in the source domain data can be applied to detection of the polyps in the second colorectal images in the target domain data, and the detection effect is equivalent to that of the colorectal images labeled with polyp information. Therefore, the phenomenon of domain migration of data during promotion of a colorectal polyp detection system is resolved, and the colorectal polyp detection system can be better promoted in the hospitals.

2. Detection of a to-be-Examined Colorectal Image

The to-be-examined colorectal image is inputted to the obtained final detection model, to obtain information about whether the to-be-examined colorectal image includes a polyp, and if the to-be-examined colorectal image includes a polyp, a type and a location of the polyp.

Figure 6:
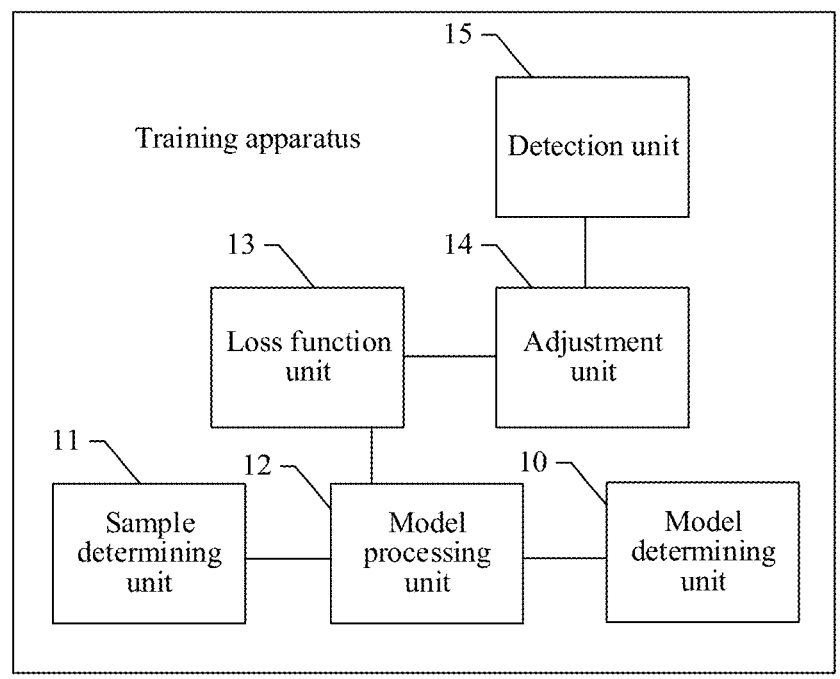
FIG. 6 is a schematic structural diagram of a training apparatus according to an embodiment of this application.

An embodiment of this application further provides a training apparatus. A schematic structural diagram of the training apparatus is shown in FIG. 6. The apparatus may further include a model determining unit 10, a sample determining unit 11, a model processing unit 12, a function loss unit 13, and an adjustment unit 14.

The model determining unit 10 is configured to determine an initial training model, the initial training model including an initial detection model and an adaptive model.

The model determining unit 10 is configured to determine that the initial detection model includes a feature extraction module and a detection and classification module, and that the adaptive model includes a domain classification module, the detection and classification module being configured to perform classification of whether a lesion target is present according to a feature extracted by the feature extraction module, the domain classification module being configured to perform domain classification according to the feature extracted by the feature extraction module; and determine an initial value of a certain parameter in the initial detection model and the adaptive model.

The feature extraction module includes an intermediate feature extraction module and a final feature extraction module, then the domain classification module is configured to perform the domain classification according to a feature extracted by the intermediate feature extraction module or the final feature extraction module. There may be one or more domain classification modules.

Moreover, the adaptive model may further include a gradient inversion module that is configured to transfer the feature extracted by the feature extraction module to the domain classification module, and is further configured to reverse, in a case that the certain parameter value is adjusted, an error of the domain classification module, to adjust the certain parameter value in the feature extraction module according to the reversed error.

The sample determining unit 11 is configured to determine a training sample, the training sample including source domain data and target domain data, the source domain data including a plurality of first user body organ images, each first user body organ image including: a first identifier of whether a lesion target is present, and a second identifier of a domain that the each first user body organ image belongs to; the target domain data including: a plurality of second user body organ images, and a third identifier of a domain that each second user body organ image belongs to.

The model processing unit 12 is configured to separately determine, according to a feature of the each first user body organ image through the initial detection model determined by the model determining unit 10, whether a lesion target is present in the each first user body organ image in the source domain data determined by the sample determining unit 11, to obtain a detection result; and separately determine a domain that each user body organ image in the training sample belongs to through the adaptive model according to a feature of the each user body organ image, to obtain a domain classification result.

The loss function unit 13 is configured to calculate a loss function value related to the initial training model according to the detection result obtained by the model processing unit 12, the domain classification result, the first identifier, the second identifier, and the third identifier.

In some embodiments, the loss function value related to the initial training model specifically includes: a function calculated value of a detection loss function and an adaptive loss function, where the detection loss function includes: a first error between information that is determined according to the initial detection model and that is about whether the lesion targets are included in the first user body organ images and the first identifier in the training sample. A third error between the types and the locations that are of the lesion targets in the some of the user body organ images and that are determined according to the initial detection model and the types and the locations of the lesion targets in the some of the user body organ images in the training sample. The adaptive loss function includes: a second error between information that is determined according to the adaptive model and that is about whether the each user body organ image in the training sample belongs to a source domain or a target domain, and the second identifier and the third identifier in the training sample.

The adjustment unit 14 is configured to adjust a certain parameter value in the initial training model according to the loss function value obtained by the loss function unit 13, to obtain a final detection model.

In some embodiments, in the training sample determined by the sample determining unit 10, for some of the first user body organ images, the some of the user body organ images include lesion targets, and the source domain data further includes types and locations of the lesion targets included in the some of the user body organ images. The model processing unit 12 is further configured to separately determine the types and the locations of the lesion targets included in the some of the user body organ images through the initial detection model, to obtain a target detection result. The loss function unit 13 is configured to calculate the loss function value related to the initial training model according to the detection result, the domain classification result, the target detection result, the first identifier, the second identifier, and the third identifier.

The adjustment unit 14 is further configured to stop adjusting the certain parameter value in a case that the adjustment to the certain parameter value meets any one of the following stop conditions: a quantity of times of the adjustment to the certain parameter value reaches a preset quantity of times; and a difference between a currently adjusted certain parameter value and a last adjusted certain parameter value is less than a threshold.

Moreover, the training apparatus in this embodiment further includes: a detection unit 15, configured to determine a to-be-examined user body organ image, and determine, according to the final detection model obtained after the adjustment unit 14 adjusts the certain parameter value, whether a lesion target is present in the to-be-examined user body organ image.

In the training apparatus of this embodiment, when a detection model used for detecting a lesion target in a user body organ image is trained, the model determining unit 10 and the sample determining unit 11 first determine that an initial training model includes an initial detection model and an adaptive model, and includes source domain data labeled with lesion target information and target domain data not labeled with lesion target information. Then, the model processing unit 12 processes data in a training sample according to the initial detection model and the adaptive model, to obtain a detection result and a domain classification result respectively. Finally, the loss function unit 13 calculates a related loss function value according to the detection result, the domain classification result, and the training sample, and the adjustment unit 14 adjusts a certain parameter value in the initial training model according to the loss function value, to obtain a final detection model. Accordingly, in a process of training the detection model, some of data of the training sample is the source domain data labeled with the lesion target information, and the remaining data of the training sample is the target domain data not labeled with the lesion target information, so that an image not labeled with the lesion target information can also be used as a training sample in a case that it is difficult to label lesion target information. Therefore, the amount of training samples is increased, and the detection model obtained through training is more accurate.

Figure 7:
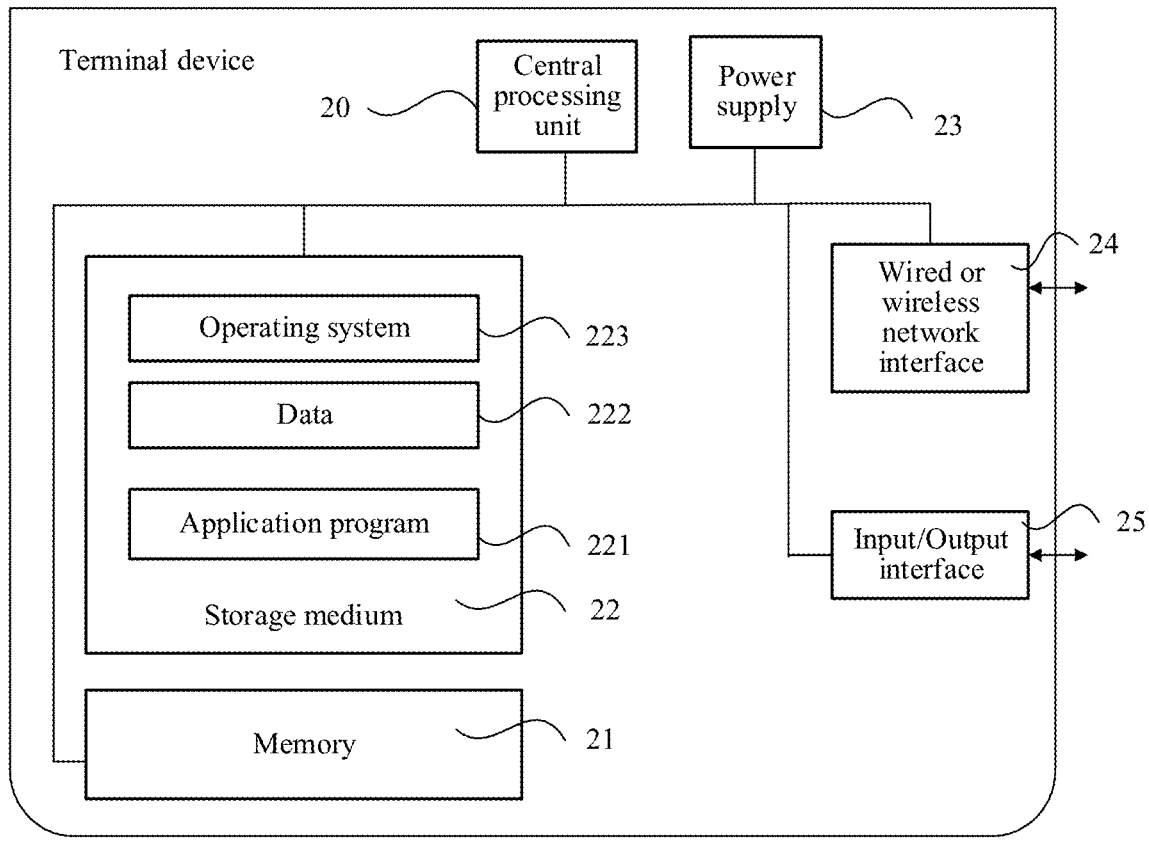
FIG. 7 is a schematic structural diagram of a terminal device according to an embodiment of this application.

An embodiment of this application further provides a terminal device. A schematic structural diagram of the terminal device is shown in FIG. 7. The terminal device may vary greatly according to different configurations or performance, and may include one or more central processing units (CPUs) 20 (for example, one or more processors), a memory 21, and one or more storage media 22 (for example, one or more mass storage devices) that store an application program 221 or data 222. The memory 21 and the storage medium 22 may be transient storage or permanent storage.

The program stored in the storage medium 22 may include one or more modules (not shown), and each module may include a series of instructions and operations for the terminal device. Further, the CPU 20 may be configured to communicate with the storage medium 22, and perform, on the terminal device, the series of instructions and operations in the storage medium 22.

In some embodiments, the application program 221 stored in the storage medium 22 includes an application program for training the detection model, and the application program may include the model determining unit 10, the sample determining unit 11, the model processing unit 12, the loss function unit 13, the adjustment unit 14, and the detection unit 15 in the foregoing training apparatus. The details are not described herein again. Further, the CPU 20 may be configured to communicate with the storage medium 22, and perform, on the terminal device, a series of operations corresponding to the application program that is stored in the storage medium 22 and that is used for training the detection model.

The terminal device may further include one or more power supplies 23, one or more wired or wireless network interfaces 24, one or more input/output interfaces 25, and/or one or more operating systems 223, for example, Windows Server™, Mac OS X™, Unix™, Linux™, or FreeBSD™.

The steps performed by the training apparatus in the foregoing method embodiment may be based on the structure of the terminal device shown in FIG. 7.

An embodiment of this application further provides a storage medium, the storage medium storing a plurality of instructions, and the instructions being adapted to be loaded by a processor to perform the detection model training method performed by the training apparatus. An embodiment of this application further provides a terminal device, including a processor and a storage medium, the processor being configured to implement instructions. The storage medium is configured to store a plurality of instructions, the instructions being loaded by a processor to perform the detection model training method performed by the training apparatus.

In some embodiments of the present disclosure, a functional unit or a functional module refers to one or more computer programs or algorithms that are developed to perform the described functions and are stored in computer readable medium. When executed by one or more processors, the computer programs may implement the functions of the corresponding functional module or functional unit. In some embodiments, a functional unit or a functional module may be implemented as hardware (e.g., processing circuitry and/or memory configured to perform the described functions). In some embodiments, a functional unit or a functional module may be implemented as a combination of software and hardware components. The software and hardware components may execute certain computer programs to implement the functions of the corresponding functional module or functional unit.

A person of ordinary skill in the art may understand that all or some of the steps of the methods in the foregoing embodiments may be implemented by a program by instructing relevant hardware. The program may be stored in a computer-readable storage medium, and the storage medium may include: a read-only memory (ROM), a random access memory (RAM), a magnetic disk, a compact disc, or the like.

The detection model training method and apparatus, and the terminal device provided in the embodiments of this application are described above in detail. Although the principles and implementations of this application are described by using specific examples in this specification, the descriptions of the foregoing embodiments are merely intended to help understand the method and the core idea of the method of this application. Meanwhile, a person skilled in the art may make modifications to the specific implementations and application range according to the idea of this application. In conclusion, the content of this specification is not to be construed as a limitation to this application.

What is claimed is:

1. A detection model training method, comprising:
   determining, by a training apparatus, an initial training model, the initial training model comprising an initial detection model and an adaptive model;
   determining, by the training apparatus, a training sample, the training sample comprising source domain data and target domain data, the source domain data comprising a plurality of first user body organ images, each first user body organ image comprising: a first identifier of whether a lesion target is present, and a second identifier of a domain that the each first user body organ image belongs to; the target domain data comprising: a plurality of second user body organ images, and a third identifier of a domain that each second user body organ image belongs to;
   determining, by the training apparatus, whether a lesion target is present in the each first user body organ image through the initial detection model according to a feature of the each first user body organ image, to obtain a detection result; and determining, by the training apparatus, a domain that each user body organ image in the training sample belongs to through the adaptive model according to a feature of the each user body organ image, to obtain a domain classification result;
   calculating, by the training apparatus, a loss function value related to the initial training model according to the detection result, the domain classification result, the first identifier, the second identifier, and the third identifier; and
   adjusting, by the training apparatus, a parameter value in the initial training model according to the loss function value, to obtain a final detection model.

2. The method according to claim 1, wherein some of the first user body organ images comprise lesion targets, and the source domain data further comprises types and locations of the lesion targets comprised in the some of the user body organ images;
   before the calculating a loss function value related to the initial training model, the method further comprises: determining, by the training apparatus, the types and the locations of the lesion targets comprised in the some of the user body organ images through the initial detection model, to obtain a target detection result; and
   the calculating a loss function value related to the initial training model further comprises: calculating the loss function value related to the initial training model according to the detection result, the domain classification result, the target detection result, the first identifier, the second identifier, and the third identifier.

3. The method according to claim 2, wherein the loss function value related to the initial training model further comprises: a function calculated value of a detection loss function and an adaptive loss function;
   the detection loss function comprises: a first error between information that is determined according to the initial detection model and that is about whether the lesion targets are comprised in the first user body organ images and the first identifier in the training sample; and a third error between the types and the locations that are of the lesion targets in the some of the user body organ images and that are determined according to the initial detection model and the types and the locations of the lesion targets in the some of the user body organ images in the training sample; and the adaptive loss function comprises: a second error between information about whether the each user body organ image in the training sample belongs to a source domain or a target domain, which is determined according to the adaptive model, and the second identifier and the third identifier in the training sample.

4. The method according to claim 1, wherein the determining, by a training apparatus, an initial training model further comprises:

determining, by the training apparatus, that the initial detection model comprises a feature extraction module and a detection and classification module, and that the adaptive model comprises a domain classification module, the detection and classification module being configured to perform classification of whether a lesion target is present according to a feature extracted by the feature extraction module, the domain classification module being configured to perform domain classification according to the feature extracted by the feature extraction module;

determining, by the training apparatus, an initial value of a parameter in the initial detection model and the adaptive model; and the adjusting, by the training apparatus, a parameter value in the initial training model according to the loss function value further comprises: adjusting, by the training apparatus, the initial value of the parameter according to the loss function value.

5. The method according to claim 4, wherein the adaptive model further comprises a gradient inversion module; and the gradient inversion module is configured to transfer the feature extracted by the feature extraction module to the domain classification module, and is further configured to reverse, if the parameter value is adjusted, an error of the domain classification module, to adjust the parameter value in the feature extraction module according to the reversed error.

6. The method according to claim 4, wherein the feature extraction module comprises an intermediate feature extraction module and a final feature extraction module, then the domain classification module is configured to perform the domain classification according to a feature extracted by the intermediate feature extraction module or the final feature extraction module; and the adaptive model comprises one or more domain classification modules.

7. The method according to claim 1, wherein the training apparatus stops adjusting the parameter value in a case that the adjustment to the parameter value meets any one of the following stop conditions:

a quantity of times of the adjustment to the parameter value reaches a preset quantity of times; and a difference between a currently adjusted parameter value and a last adjusted parameter value is less than a threshold.

8. The method according to claim 1, comprising:

determining, by the training apparatus, a to-be-examined user body organ image, and determining, according to the final detection model, whether a lesion target is present in the to-be-examined user body organ image.

9. A non-transitory storage medium, the storage medium storing a plurality of instructions, the instructions being adapted to be loaded by a processor and causing the processor to determine an initial training model, the initial training model comprising an initial detection model and an adaptive model;

determine a training sample, the training sample comprising source domain data and target domain data, the source domain data comprising a plurality of first user body organ images, each first user body organ image comprising: a first identifier of whether a lesion target is present, and a second identifier of a domain that the each first user body organ image belongs to; the target domain data comprising: a plurality of second user body organ images, and a third identifier of a domain that each second user body organ image belongs to;

separately determine whether a lesion target is present in the each first user body organ image through the initial detection model according to a feature of the each first user body organ image, to obtain a detection result; and separately determine a domain that each user body organ image in the training sample belongs to through the adaptive model according to a feature of the each user body organ image, to obtain a domain classification result;

calculate a loss function value related to the initial training model according to the detection result, the domain classification result, the first identifier, the second identifier, and the third identifier; and adjust a parameter value in the initial training model according to the loss function value, to obtain a final detection model.

10. The storage medium according to claim 9, wherein in the training sample, some of the first user body organ images comprise lesion targets, and the source domain data further comprises types and locations of the lesion targets comprised in the some of the user body organ images;

the instructions further cause the processor to separately determine the types and the locations of the lesion targets comprised in the some of the user body organ images through the initial detection model, to obtain a target detection result; and calculate the loss function value related to the initial training model according to the detection result, the domain classification result, the target detection result, the first identifier, the second identifier, and the third identifier.

11. The storage medium according to claim 10, wherein the loss function value related to the initial training model further comprises: a function calculated value of a detection loss function and an adaptive loss function;

the detection loss function comprises: a first error between information that is determined according to the initial detection model and that is about whether the lesion targets are comprised in the first user body organ images and the first identifier in the training sample; and a third error between the types and the locations that are of the lesion targets in the some of the user body organ images and that are determined according to the initial detection model and the types and the locations of the lesion targets in the some of the user body organ images in the training sample; and the adaptive loss function comprises: a second error between information that is determined according to the adaptive model and that is about whether the each user body organ image in the training sample belongs to a source domain or a target domain, and the second identifier and the third identifier in the training sample.

12. The storage medium according to claim 9, wherein the instructions further cause the processor to determine that the initial detection model comprises a feature extraction module and a detection and classification module, and that the adaptive model comprises a domain classification module, the detection and classification module being configured to perform classification of whether a lesion target is present according to a feature extracted by the feature extraction module, the domain classification module being configured to perform domain classification according to the feature extracted by the feature extraction module; and determine an initial value of a parameter in the initial detection model and the adaptive model.

13. A terminal device, comprising a processor and a storage medium, the processor being configured to implement instructions; and
the storage medium being configured to store a plurality of instructions, the instructions being loaded by the processor to perform the detection model training method, comprising:
determining an initial training model, the initial training model comprising an initial detection model and an adaptive model;
determining a training sample, the training sample comprising source domain data and target domain data, the source domain data comprising a plurality of first user body organ images, each first user body organ image comprising: a first identifier of whether a lesion target is present, and a second identifier of a domain that the each first user body organ image belongs to; the target domain data comprising: a plurality of second user body organ images, and a third identifier of a domain that each second user body organ image belongs to;
determining whether a lesion target is present in the each first user body organ image through the initial detection model according to a feature of the each first user body organ image, to obtain a detection result; and determining a domain that each user body organ image in the training sample belongs to through the adaptive model according to a feature of the each user body organ image, to obtain a domain classification result;
calculating a loss function value related to the initial training model according to the detection result, the domain classification result, the first identifier, the second identifier, and the third identifier; and
adjusting a parameter value in the initial training model according to the loss function value, to obtain a final detection model.

14. The terminal device according to claim 13, wherein some of the first user body organ images comprise lesion targets, and the source domain data further comprises types and locations of the lesion targets comprised in the some of the user body organ images;
before the calculating a loss function value related to the initial training model, the method further comprises: determining the types and the locations of the lesion targets comprised in the some of the user body organ images through the initial detection model, to obtain a target detection result; and the calculating a loss function value related to the initial training model further comprises: calculating the loss function value related to the initial training model according to the detection result, the domain classification result, the target detection result, the first identifier, the second identifier, and the third identifier.

15. The terminal device according to claim 14, wherein the loss function value related to the initial training model further comprises: a function calculated value of a detection loss function and an adaptive loss function;
the detection loss function comprises: a first error between information that is determined according to the initial detection model and that is about whether the lesion targets are comprised in the first user body organ images and the first identifier in the training sample; and a third error between the types and the locations that are of the lesion targets in the some of the user body organ images and that are determined according to the initial detection model and the types and the locations of the lesion targets in the some of the user body organ images in the training sample; and
the adaptive loss function comprises: a second error between information about whether the each user body organ image in the training sample belongs to a source domain or a target domain, which is determined according to the adaptive model, and the second identifier and the third identifier in the training sample.

16. The terminal device according to claim 13, wherein the determining, by a training apparatus, an initial training model further comprises:
determining that the initial detection model comprises a feature extraction module and a detection and classification module, and that the adaptive model comprises a domain classification module, the detection and classification module being configured to perform classification of whether a lesion target is present according to a feature extracted by the feature extraction module, the domain classification module being configured to perform domain classification according to the feature extracted by the feature extraction module;
determining an initial value of a parameter in the initial detection model and the adaptive model; and
the adjusting a parameter value in the initial training model according to the loss function value further comprises: adjusting the initial value of the parameter according to the loss function value.

17. The terminal device according to claim 16, wherein the adaptive model further comprises a gradient inversion module; and
the gradient inversion module is configured to transfer the feature extracted by the feature extraction module to the domain classification module, and is further configured to reverse, if the parameter value is adjusted, an error of the domain classification module, to adjust the parameter value in the feature extraction module according to the reversed error.

18. The terminal device according to claim 16, wherein the feature extraction module comprises an intermediate feature extraction module and a final feature extraction module, then the domain classification module is configured to perform the domain classification according to a feature extracted by the intermediate feature extraction module or the final feature extraction module; and
the adaptive model comprises one or more domain classification modules.

19. The terminal device according to claim 13, wherein the training apparatus stops adjusting the parameter value in a case that the adjustment to the parameter value meets any one of the following stop conditions:
   a quantity of times of the adjustment to the parameter value reaches a preset quantity of times; and
   a difference between a currently adjusted parameter value and a last adjusted parameter value is less than a threshold.

20. The terminal device according to claim 13, the detection model training method further comprising:
   determining a to-be-examined user body organ image, and determining, according to the final detection model, whether a lesion target is present in the to-be-examined user body organ image.

* * * * *